(12) United States Patent
Hollingsworth et al.

(10) Patent No.: US 7,579,343 B2
(45) Date of Patent: Aug. 25, 2009

(54) PYRROLO-THIAZINES AND PROCESSES FOR THE PREPARATION AND USE THEREOF

(75) Inventors: Rawle Hollingsworth, Haslett, MI (US); Li Gao, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 389 days.

(21) Appl. No.: 11/516,317

(22) Filed: Sep. 6, 2006

(65) Prior Publication Data

US 2007/0055062 A1   Mar. 8, 2007

Related U.S. Application Data (60) Provisional application No. 60/715,395, filed on Sep. 8, 2005.

(51) Int. Cl.
*C07D 513/04*   (2006.01)
*C07D 513/14*   (2006.01)
*A61K 31/542*   (2006.01)

(52) U.S. Cl. ................. 514/224.2; 544/32; 544/47; 514/224.5

(58) Field of Classification Search ............... 544/32, 544/47; 514/224.5, 224.2
See application file for complete search history.

*Primary Examiner*—Kahsay T Habte
(74) *Attorney, Agent, or Firm*—Ian C. McLeod (57) ABSTRACT

1H-Pyrrolo-1,4-thiazines and a process for the preparation thereof are described. These compounds are useful as enzyme inhibitors in cells, particularly for medical uses.

14 Claims, 8 Drawing Sheets

Chair ($^4C_1$)  FIGURE 1A

Skew boat ($^1S_3$)  FIGURE 1B

Boat ($^{1,4}B$)  FIGURE 1C

β-D-*Ribo*-　　　　　　　α-L-*Lyxo*

FIGURE 9B

PYRROLO-THIAZINES AND PROCESSES FOR THE PREPARATION AND USE THEREOF

CROSS-REFERENCE TO RELATED APPLICATIONS

This application claims the benefit of Provisional Application No. 60/715,395, filed Sep. 8, 2005, which is incorporated herein by reference in its entirety.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to novel pyrrolo thiazines, particularly comprising benzothiazines, which are enzyme inhibitors and useful for inhibiting growth of cells containing the enzymes in vivo. In particular, the present invention relates to pyrrolo-thiazines which are ribosidase inhibitors.

(2) Description of the Related Art

The prior art does not describe the compounds of the present invention. The general prior art is described hereinafter in the context of the invention.

Objects

It is an object of the present invention to provide novel pyrrolo-thiazines for use as enzyme inhibitors. In particular, the present invention relates to the use of these compounds which are ribosidase inhibitors. Further, the present invention relates to a process for the preparation of the pyrrolo-thiazines.

These and other objects will become increasingly apparent by reference to the following description.

SUMMARY OF THE INVENTION

The present invention relates to a compound of the formula wherein $R_1$ and $R_2$ separately are selected from the group consisting of hydrogen, alkyl containing 1 to 6 carbon atoms which can be substituted or unsubstituted with O, N, S and halogen containing groups, and $R_1$ and $R_2$ together form a ring group containing 6 carbon atoms in the ring which can be substituted with O, N, S and halogen containing groups (Br, Cl, F, I). Further, the present invention relates to the compound wherein the ring group is a benzene ring. In particular the compounds are 3,4-dihydroxy,2,3,3a-4'-tetrahydro-1-H-pyrrolo-[2,1c][1,4]benzothiazine; 2(S), 3(R), 4(S)-3,4-dihydroxy-1,3,3a,4-tetrahydro-1H-pyrrolo-[2,1-c][1,4]benzothiazine (6); 2(R)-3(R),4(S)-3,4-dihydroxy-2,3,3a,4-tetrahydro-1H-pyrrolo-[2,1-c][1,4]benzothiazine (7); or 7(S)-8(R),9(S)-3,4-dihydroxy-hexahydro-1H-pyrrolo[1,4]-thiazine (8).

The present invention also relates to a process for the preparation of a compound which is a 1H-pyrrolo-1,4-thiazine which comprises: reacting 5-bromo-5-deoxy-2,3-di-O-protected-4-pentulosonic acid methyl ester with 2-aminothiophenol or 2-aminothioethane in a solvent containing a reducing agent to produce a protected pyrrolo-1,4-thiazine; and deprotecting the protected pyrrolo 1,4-thiazine to produce the 1H-pyrrolo-1,4-thiazine.

Preferably the reaction is at a temperature between about 0° and 100° C. Preferably the pentulosonic and methyl ester is derived from ribose. Preferably the compound is 3,4-dihydroxy,2,3,3a-4'-tetrahydro-1H-pyrrolo-[2,1c][1,4]benzothiazine. Most preferably, the compound is 2(S), 3(R), 4(S)-3,4-dihydroxy-1,3,3a,4-tetrahydro-1H-pyrrolo-[2,1-c][1,4]benzothiazine (6). Also preferably, the compound is 2(R)-3(R),4(S)-dihydroxy-2,3,3a,4-tetrahydro-1H-pyrrolo-[2,1-c][1,4]benzothiazine (7). The compound also is 7(S)-8(R),9(S)-3,4-dihydroxy-hexahydro-1H-pyrrolo[1,4]-thiazine (8).

The present invention also relates to a method of inhibiting growth of cells by inhibiting an enzyme which comprises administering to the cells an effective amount of a compound of the formula wherein $R_1$ and $R_2$ separately are selected from the group consisting of hydrogen, alkyl containing 1 to 6 carbon atoms which can be substituted or unsubstituted with O, N, S and halogen containing groups, and $R_1$, and $R_2$ together form a ring group containing 6 carbon atoms in the ring which can be substituted with O, N, S and halogen containing groups (Br, Cl, F, I).

Preferably the cells are microorganisms. Also preferably the cells are tumor cells. Preferably the enzyme is a ribosidase.

The present invention also relates to a composition which comprises a compound of the formula wherein $R_1$ and $R_2$ separately are selected from the group consisting of hydrogen, alkyl containing 1 to 6 carbon atoms which can be substituted or unsubstituted with O, N, S and halogen containing groups, and $R_1$, and $R_2$ together form a ring group containing 6 carbon atoms in the ring which can be substituted with O, N, S and halogen containing groups (Br, Cl, F, I), with a pharmaceutical carrier.

The present invention further provides a pharmaceutical composition which comprises one or more compounds according to the above formulae and a pharmaceutically acceptable carrier, diluent, or excipient. Thus, the compound may be used in the manufacture of a medicament. Pharmaceutical compositions of the compound synthesizes as described herein can be formulated as solutions or lyophilized powders for parenteral administration. The powders can be reconstituted by addition of a suitable diluent or other pharmaceutically acceptable carrier prior to use. The liquid formulation can be a buffered, isotonic, aqueous solution. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insulation. In particular embodiments, it can be desirable to further add one or more excipients selected from the group consisting of polyvinylpyrrolidone, gelatin, hydroxyl cellulose, acacia, polyethylene glycol, mannitol, sodium chloride, and sodium citrate.

Alternately, one or more of the above compounds may be encapsulated, tableted or prepared in an emulsion or syrup for oral administration. Pharmaceutically acceptable solid or liquid carrier can be added to enhance or stabilize the composition, or to facilitate preparation of the composition. Solid carriers include starch, lactose, calcium sulfate dihydrate, terra alba, magnesium stearate or stearic acid, talc, pectin, acacia, agar, or gelatin. Liquid carriers include syrup, peanut oil, olive oil, saline, and water. The carrier can also include a sustained release material such as glyceryl monostearate or glyceryl distearate, alone or with a wax. The pharmaceutical preparations are made following the conventional techniques of pharmacy such as milling, mixing, granulating, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation can be administered directly or filled into a soft gelatin capsule.

For rectal administration, one or more of the above compounds can also e combined with excipients such as cocoa butter, glycerin, gelatin, or polyethylene glycols and molded into a suppository.

The methods of the present invention further include topical administration of one or more of the above compounds. By topical administration is meant non-systemic administration, including the application of a compound of the invention externally to the epidermis, to the buccal cavity, and instillation into the ear, eye, and nose, wherein the compound does not significantly enter the blood stream. By systemic administration is meant oral, intravenous, intraperitoneal, and intramuscular administration. The amount of a compound of the invention required for therapeutic or prophylactic effect upon topical administration will, of course, vary with the compound chosen, the nature and severity of the condition being treated and the animal or human undergoing treatment, and is ultimately at the discretion of the physician.

The topical formulations of the present invention, both for veterinary and for human medical use, comprise one or more of the above compounds together with one or more acceptable carriers thereof, and optionally any other therapeutic ingredients.

Formulations suitable for topical administration include liquid or semi-liquid preparations suitable for penetration through the skin to the site of where treatment is required such as: liniments, lotions, creams, ointments, or pastes, and drops suitable for administration to the eye, ear, or nose.

Drops according to the present invention may comprise sterile aqueous or oily solutions or suspensions and may be prepared by dissolving one or more of the above compounds in a suitable aqueous solution of a bactericidal and/or fungicidal agent and/or any other suitable preservative, and preferably including a surface active agent. The resulting solution can then be clarified by filtration, transferred to a suitable container which is then sealed and sterilized by autoclaving or maintaining at 90-100° C. for half an hour. Alternatively, the solution can be sterilized by filtration and transferred to the container by an aseptic technique. Examples of bactericidal and fungicidal agents suitable for inclusion in the drops are phenylmercuric nitrate of acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion can comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments, or pastes according to the present invention are semi-solid formulations of the active ingredient for external application. They may be made by mixing the compound in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active agent such as sorbitan esters or polyoxyethylene derivatives thereof. Suspending agents such as natural gums, cellulose derivatives or in organic materials such as silicaceous silicas, and other ingredients such as lanolin, may also be included.

DESCRIPTION OF THE PREFERRED EMBODIMENTS

All patents, patent applications, government publications, government regulations, and literature references cited in this specification are hereby incorporated herein by reference in their entirety. In case of conflict, the present description, including definitions, will control.

The present invention particularly relates to the preparation and evaluation of dihydroxy-tetrahydro-1H-pyrrolo-[2,1-c][1,4]benzothiazines as conformationally restricted transition state inhibitors of β-ribosidases.

The preparation of 3 new chiral thiazines from ribose is described. Two of these are dihydroxy-tetrahydro-1H-pyrrolo-[2,1-c][1,4]benzothiazines with iminopentitol substructures corresponding to the L-lyxo and D-ribo configurations. The compounds were designed to present a favorable transition state mimic for the inhibition of ribosidases by restricting the iminopentitol scaffold to conformations close to the most desirable conformation as suggested by stereoelectronic configurations (antiperiplanar lone pair requirement). Conformations were evaluated by X-ray analysis. The compounds demonstrated good inhibitory activity against β-D-ribosidases present in bacterial cells and cell lysates. The inhibitory activity of the more readily formed but unnatural L-lyxo isomer was comparable to that of the isomer with the natural D-ribo configuration. The aromatic ring provides further enhancements for the inclusion of more interacting substituents. This new thiazine class opens the way to the development of new inhibitors to carbohydrate processing enzymes of therapeutic importance such as nucleoside hydrolases and purine nucleoside phosphorylases (PNP).

Stereochemical considerations in the design of inhibitors of glycosidases are important elements. Glycosides are invariably acetals or aminals in the case of N-glycosides such as nucleosides. Nucleoside hydrolases are especially important because they are found in several pathogens such as protozoa[1] and bacteria[2] but not in mammalian systems and are therefore excellent drug targets. The purine salvage pathway of parasitic protozoa is especially targeted because these organisms cannot synthesize purines de novo.

Figure 1A:
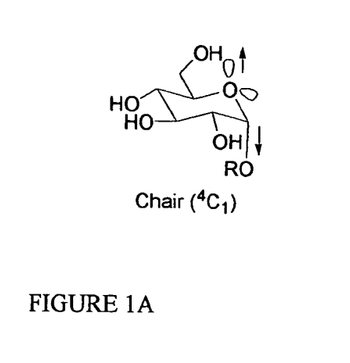
FIGS. 1A to 1C are drawings of chair, skew and boat conformations allowing anti-periplanar orientation of aglycon fragment and a doubly occupied non-bonding orbital in α- and β-D-glycopyranosides.
Figure 1B:
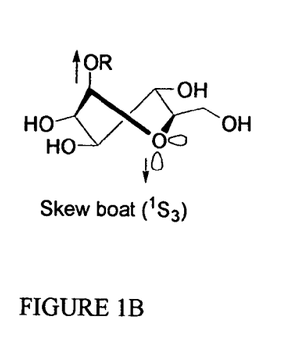
Figure 1C:
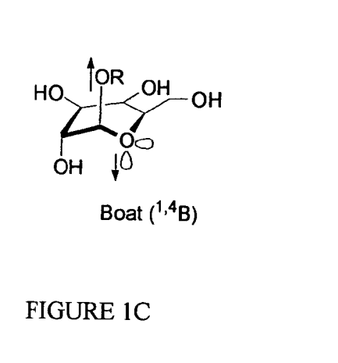

Stereoelectronic control in the hydrolysis of acetals and aminals requires that the ligand leaving the tetrahedral center be aligned anti-periplanar to a doubly occupied non-bonding orbital (electron lone pair).[3] This requirement has been largely borne out by observations on the structure of molecules that inhibit -D-glycosides and -D-glycosides. It is generally held that the cleavage of glycosidic linkages proceeds via an oxocarbenium type intermediate and that the stereoelectronic requirements for the formation of this species can be met via a chair shaped transition state in the case of -D-glycopyranosides and either a skew boat or a boat conformation for the corresponding -anomers.[4,5] The chair, skew and boat conformations are illustrated for -and -D-glucopyranosides in FIG. 1.

Figure 2:
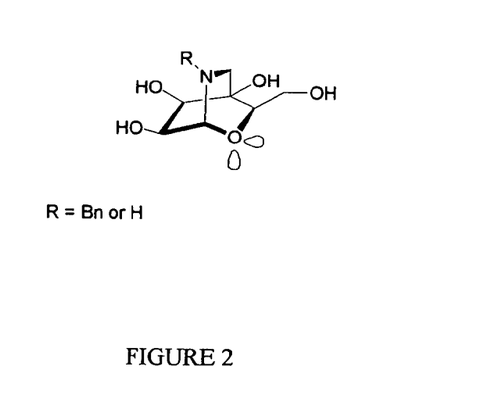
FIG. 2 is a drawing of polyhydroxylated isoquinuclidines that mimic the boat conformation proposed for transition states of β-glycopyranosides undergoing glycosidic cleavage.

In support of this conclusion, polyhydroxylated isoquinuclidines that mimic the boat conformation that allows antiperiplanar alignment of the leaving group and one lone pair on the ring oxygen of pyranosides have been prepared and tested (FIG. 2). These have been shown to be strong and selective inhibitors of β-mannosidase enzymes.[6]

The polyhydroxylated isoquinuclidines inhibited snail and jack bean β-mannosidases. $IC_{50}$ values ranged from 0.69 to 20 mM depending on the inhibitor-enzyme pair. Ribofuranosides with the β-D-configuration are central to the biochemistry of living systems. This configuration characterizes nucleic acids, nucleosides and nucleotides as well as their 2'-deoxy analogs.

Many biochemical transformations go through the same putative oxocarbenium transition state as ribosidase catalyzed hydrolysis of ribosides. Some examples of the many important processes involving the formation or transformation of β-D ribofuranosides are shown in Scheme 1. They are N-glycanases including nucleoside hydrolases,[7-9] hypoxanthine-guanine phosphoribosyltransferases (HGPRTases)[10] and purine nucleoside phosphorylases (PNP).[11-14]

Scheme 1. Examples of nucleoside/nucleotide enzymatic transformations involving oxocarbenium intermediates and the formation or transformation of a β-D-furanoside. HGPRT is a hypoxanthine guanine phosphoribosyl transferase. PNP is a purine nucleoside phosphorylase. Nucleoside hydrolases can also depurinate nucleic acid chains. This is the case in ribosome inactivating proteins (RIPs).

Iminopentitols are ground state analogs of intermediate/transition state species in the cleavage of glycosidic linkages of ribosides where the oxocarbenium charge is mimicked by the protonated nitrogen. Examples of ribo iminopentitols that have been successfully used as inhibitors are immucillin-H (1) and its derivative (2).[15,16] Naturally occurring iminopentitols that have the D-ribo (3) as well as L and D-arabino configurations (4 and 5 respectively) have been isolated from several sources.[17-20]

Figure 3A:
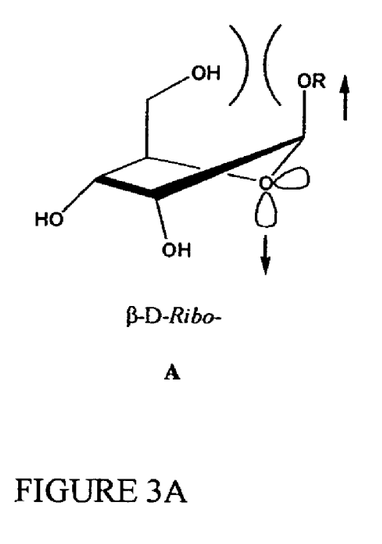
FIGS. 3A and 3B are drawings of favorable conformations for transition state structures of β-D-ribofuranosides (A), and α-L-lyxofuranosides (B) in which the aglycon fragment is anti-periplanar with one doubly occupied non-bonding orbital.
Figure 3B:
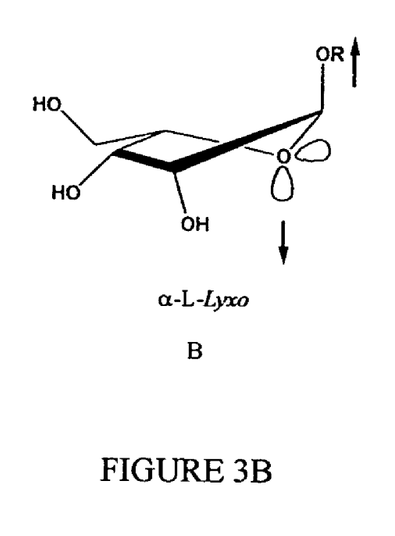

The stereoelectronic control of β-D-ribosidase hydrolysis or aglycon displacement requires an unfavorable alignment of the hydroxymethyl group with the departing alkoxy group at C1 (FIG. 3A). In the case of nucleoside derivatives the departing alkoxy group is, of course, replaced by a nitrogen functionality that is part of a heterocyclic base. The same antiperiplanar arrangement of leaving group and electron lone pair is still required. Such a conformation is untenable without a large energy penalty for β-D-ribosides but can be readily formed by α-L-lyxosides (FIG. 3B). A very potent inhibitor might be one with the α-L-lyxo configuration locked in the appropriate conformation. Such an inhibitor might be as effective as or even more effective than the cor- responding D-ribo analog despite the fact that it is a member of the unnatural L-Series. A β-D-riboside constrained in the conformation shown in FIG. 3A would also be an effective inhibitor but would be more of a synthetic challenge because of the structural constraints.

Most synthetic methods that yield the iminopentitol ring under equilibrium conditions that allow the formation of either the D-ribo or the L-lyxo compound would yield the latter predominantly or exclusively. It would also be of great interest if this more accessible isomer had useful inhibitory properties.

The synthesis and preliminary evaluation of the ribosidase inhibition activity of two tricyclic systems containing an iminopentitol moiety with the α-L-lyxo- and β-D-ribo-configurations are described. The systems are 2(S)-3(R),4(S)-3,4-dihydroxy-2,3,3a,4-tetrahydro-1H-pyrrolo-[2,1-c][1,4]benzothiazine (6) and 2(R)-3(R),4(S)-3,4-dihydroxy-2,3,3a,4-tetrahydro-1H-pyrrolo-[2,1-c][1,4]benzothiazine (7). In the α-L-lyxo compound (6) the iminopentitol moiety is conformationally restricted so that a would-be leaving group would be close to the anti-periplanar orientation to the ring nitrogen lone pair. The antiperiplanar arrangement can then be met with a slight change of orientation of the aglycon instead of a complete (energetically unfavorable) ring inversion. A similar situation occurs in the case of the β-D-ribo compound 7, but there is greater flexibility in the sugar ring. Compounds 6 and 7 also contain an aromatic ring that can be used to attach leaving group surrogates at an appropriate point away from the anomeric center. Further derivitization of this aromatic group can provide additional points for H-bonding and other favorable contacts with the enzyme. A less conformationally constrained analog with the α-L-lyxo-configuration (8) lacking the aromatic ring was also prepared and evaluated.

6

7

8

Figure 4:
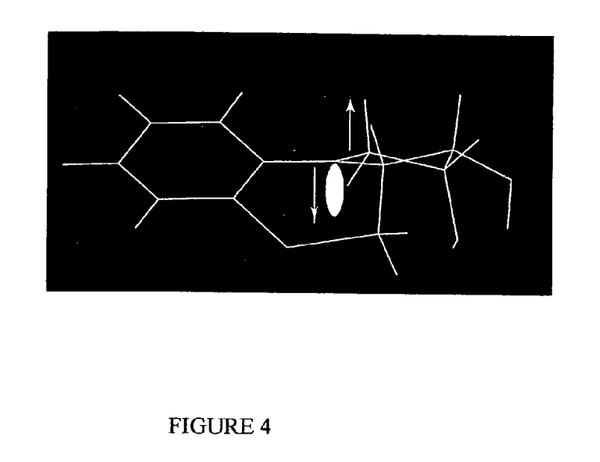
FIG. 4 is a drawing of 1(S),2(R),3(S)-dihydroxy-2,3,3a,4-tetrahydro-1H-pyrrolo-[2,1-c][1,4]benzothiazine (6). The geometry in this molecular model is MM3 optimized. The arrows indicate the orientations of the hydrogen that occupies the position normally occupied by the leaving group and the orientation of the electron lone pair on the nitrogen atom (white ellipsoid).

Molecular models of compound 6 and 7 showing the near antiperiplanar arrangement of the C1 hydrogen that occupies the near-axial position and the lone pair on the nitrogen atom are shown in FIG. 4.

The strategy chosen for the synthesis is outlined in Scheme 2. It is based on the reaction of an α-aminothiol with a 5-bromo-5-deoxy-4-ulosonic acid with the D-erythro configuration which is prepared by the oxidation of methyl 2,3-di-O-acetyl-5-bromo-5-deoxy-β-D-ribofuranoside with chromium trioxide.

-continued

+ isomer

Scheme 2: i. HCl/MeOH; ii. Ph$_3$P, CBr$_4$, pyridine, 86.7% for 2 steps; iii PivCl, pyridine, 91.1%; iv. CrO$_3$, Ac$_2$O, HOAC, 96.6%; v (1) 2-aminothiophenol, CH$_3$OH; (2) NaCNBH$_3$, CH$_3$OH; (3) Na$_2$CO$_3$, CH$_2$Cl$_2$, 67% for 2 steps; vi (1) HS(CH$_2$)$_2$NH$_2$, CH$_3$OH; (2) NaCNBH$_3$, CF$_3$COOH, 57% for 2 steps; vii (1) BH$_3$-THF; (2) NaOCH$_3$, CH$_3$OH, 91% for 2 steps for preparation of 6, 87% for 7 and 85% for preparation of 8.

Although there is no precedent for the oxidation of bromo glycosides by this method, the oxidation of peracylated β-glycosides is known to give ulosonic acids in good yield.[21,22] Displacement of the bromo group of the ulosonic acid ester with the sulfur group of an α-aminothiol followed by reduction of the intermediate imine or aminal formed by reaction of the amino group onto the carbonyl with cyanoborohydride produces a thiomorpholine ring. The amino group reacts intramolecularly with the ester group to form a lactam. The desired products are obtained by reduction of the lactam with borane followed by deacylation.

The hydrolysis of β-riboside under catalysis by β-ribosidases features an oxocarbenium ion transition state, similar to nucleoside hydrolases, nucleoside phosphorylases and related enzymes. The β-ribosidase inhibitory properties of 6, 7 and 8 were evaluated using 3',4'-dihydroxyflavone-4'-β-D-ribofuranoside 16 (DHF-riboside) as the substrate and bacterial lysates or whole cells as the source of β-ribosidase. The hydrolysis of this chromogenic substrate can be catalyzed by β-ribosidases to release 3',4'-dihydroxyflavone, which forms a highly colored chelate with iron.[23]

16

The synthetic strategy for preparing 2(S)-3(R),4(S)-3,4-dihydroxy-2,3,3a,4-tetrahydro-1H-pyrrolo-[2,1-c][1,4]benzothiazine (6) and its diasteriomer 7 was achieved in the following Examples. Treatment of the 5-bromo-5-deoxy-4-ulosonic acid methyl ester with aminothiophenol, followed by reduction, cyclization and deprotection yielded the lactam product with the L-lyxo configuration (6) in a yield that was 5 times greater than that of the corresponding D-ribo isomer (7). The isomers could be readily identified by the coupling constants of the signals for the 3-protons in NMR spectra. The L-lyxo compound was characterized by a small (~3 Hz) coupling constant between the H2 and H3 signals of the tetrahydropyrrole ring. The identification of the L-lyxo isomer was confirmed by X-ray analyses of the reduced products.

The same sequence using aminoethanethiol instead of aminothiophenol yielded 7(S)-8(R),9(S)-dihydroxy-hexahydro-1H-pyrrolo-[1,4]-thiazine (8) in 85% yield from the corresponding (L-lyxo) lactam which was obtained in 57% yield. The isomeric lactam, some uncyclized amino ester and an intermediate imine were the other products obtained in the formation of the lactam. The L-lyxo product was obtained in a yield that was 3 times that of the isomeric D-ribo product.

Figure 5A:
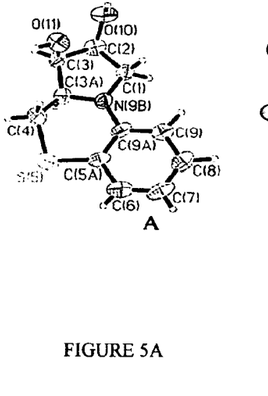
FIGS. 5A, 5B and 5C are drawings of X-ray structures of Compound 6.
Figure 5B:
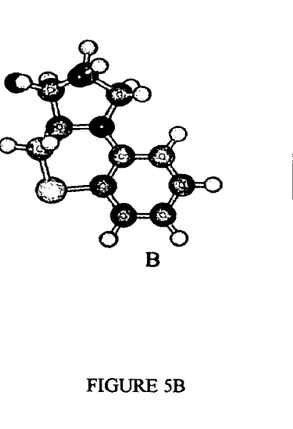

The calculated conformation of the tetrahydro-1H-pyrrolo-[2,1-c][1,4]benzothiazine (6) agreed very well with the calculated structure. A comparison of the two structures is shown in (FIG. 5A and 5B). The conformation of the more simple bicyclic system 8 was expected to be similar to that of 6 except that greater freedom in the conformation that the thiomorpholine nucleus could take is expected since it is no longer fused to a rigid aromatic ring.

Figure 5C:
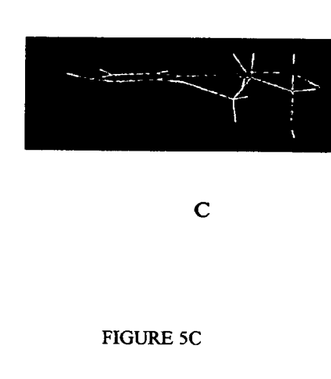

FIG. 5A shows Ortep drawing of the X-ray structure of the tetrahydro-1H-pyrrolo-[2,1-c][1,4]benzothiazine (6) compared to the MM3 geometry optimized calculated structure (FIG. 5B). The hydroxyl groups which are free to rotate are in slightly different orientations but the ring geometries are the same. The angles at the ring junctions are practically identical. FIG. 5C shows another orientation of the X-ray structure of 6.

Figure 6:
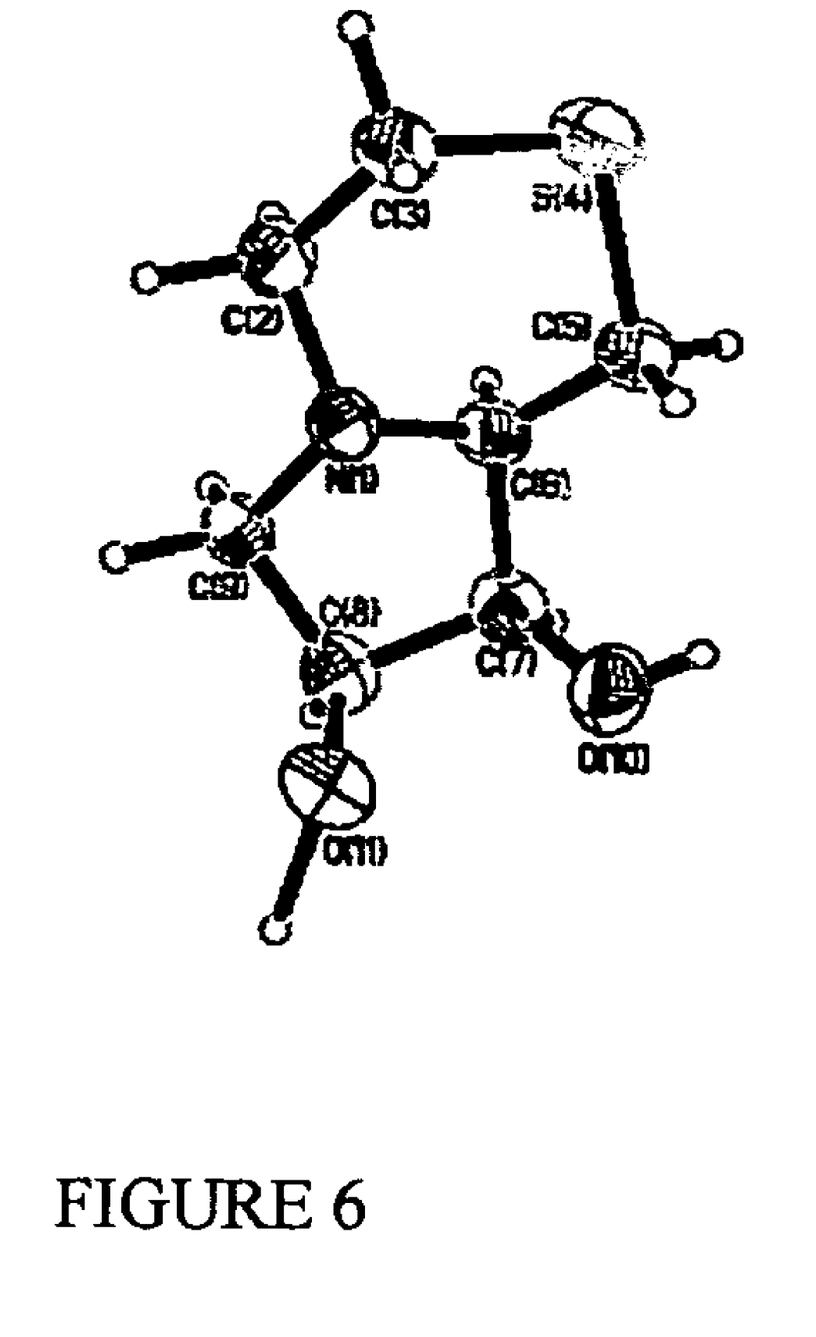
FIG. 6 is an Ortep drawing of the X-ray structure of compound 8.

The X-ray structure of 8 is shown in FIG. 6.

FIG. 6 is an Ortep drawing of the X-ray structure of the hexahydro-1H-pyrrolo-[1,4]-thiazine (8)

Figure 7A:
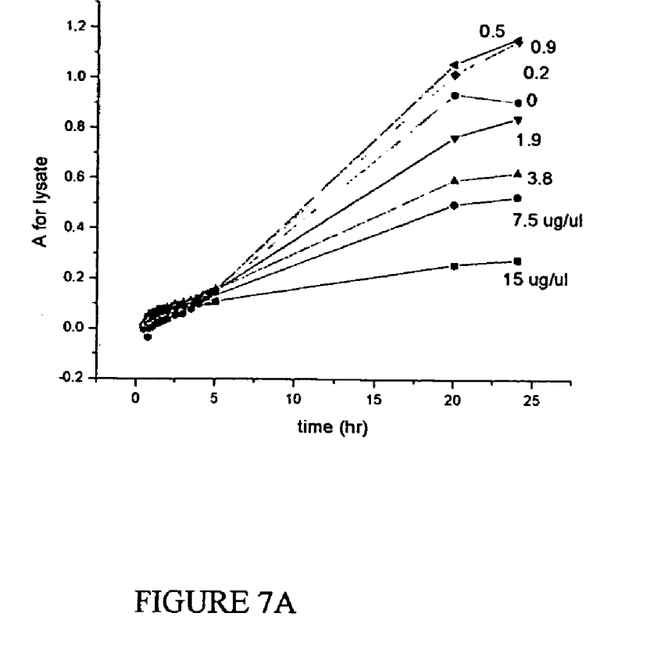
FIGS. 7A and 7B are graphs of absorbance assays versus time for compounds 6 and 7.
Figure 7B:
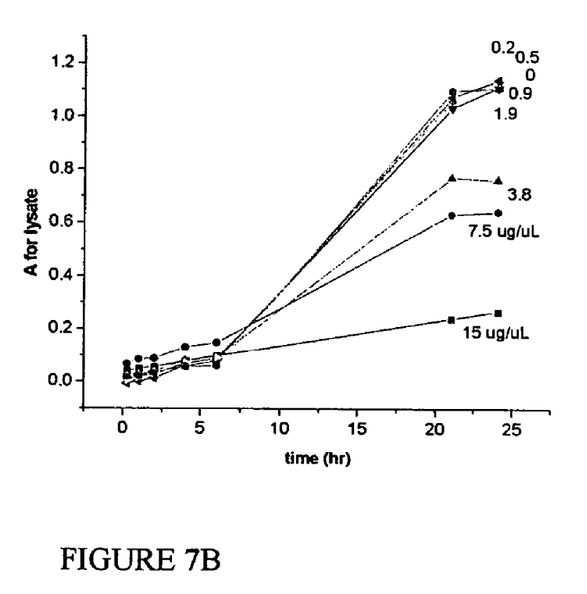

Compounds 6-8 were evaluated for their ability to inhibit the action of β-ribosidases produced by Gram negative bacteria. There are no commercially available β-ribosidases and it is the usual course to use intrinsic ribosidase activities from actual bacteria or bacterial cell lysates. Ribosidase inhibition assays were performed using Salmonella sp.35664 to produce β-ribosidase enzymes. Both whole cells and lysed bacteria were tested. Ribosidase activity is indicated by a purple color formed by complexation of the freed phenol with ferric ions. FIGS. 7A and 7B are (7A) absorbance of the assay mixture produced by a lysate of Salmonella sp.35664 with 3',4'-dihydroxyflavone-4'-β-D-ribofuranoside in the presence of 6 in concentrations from 0 to 15 μg/μL over a 24 hour period. (7B) Absorbance of the assay mixture in the presence of 7. Note that the differences in inhibition between the two are marginal at higher inhibitor concentrations. Note also that in both cases there is a threshold value of 0.9 µg/µL for the inhibitor concentration over which no inhibition is observed. The more inhibition of the enzyme, the less cleavage of the substrate.

Figure 8A:
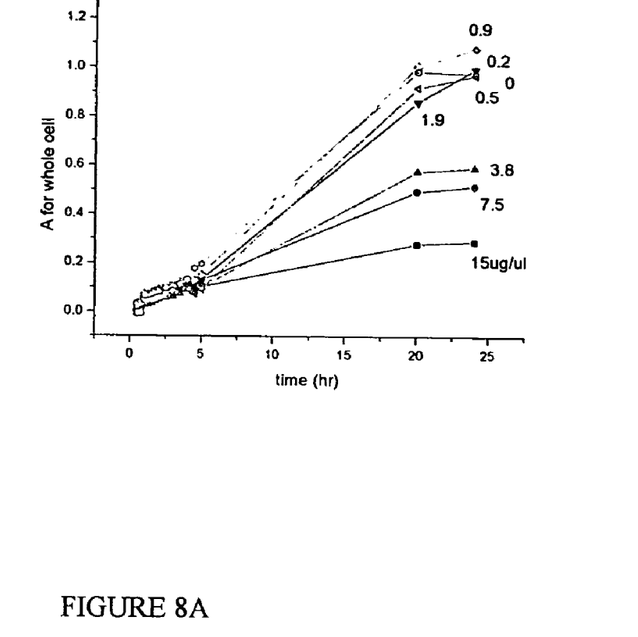
FIGS. 8A and 8B are graphs of an assay of absorbance versus time.
Figure 8B:
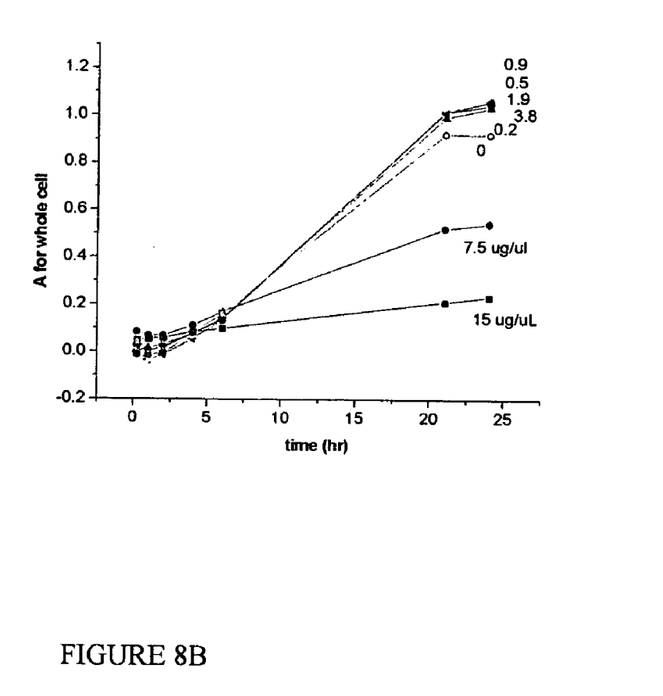

FIG. 8A shows absorbance of the assay mixture produced by whole cells of *Salmonella* sp.35664 with 3',4'-dihydroxyflavone-4'-β-D-ribofuranoside in the presence of 6 in concentrations from 0 to 15 µg/µL over a 24 hour period. FIG. 8B shows absorbance of the assay mixture in the presence of 7. No inhibition is observed between 0 and 1.9 µg/µL indicating that there might be uptake limitations. In the case of compound 7, no inhibition is also observed for the 3.8 µg/µL inhibitor concentration. There are only minor differences for the inhibitory properties of the two compounds at the higher concentrations.

FIGS. 8A and 8B are similar plots for the whole cell assay using the same bacterial strain. The results show that the L-lyxo analog has good inhibitory activity against β-ribosidases produced from this strain. About 70% inhibition at concentration 15 µg/µL (67 mM) at 24 hours for both whole cell and lysate was observed. Fifty percent inhibition was observed at a concentration 7.5 µg/µL. The inhibition activity was comparable to that of the D-ribo analog (7). The simpler bicyclic system 8 showed no significant inhibition for the β-ribosidase(s) produced by *Salmonella* sp.35664. It is important to note that there may be more than one ribosidase activity in *Salmonella* sp.35664 and that an even better inhibitory activity might be obtained for any one specific purified enzyme. Some abrupt changes in the slope of the inhibition curve suggest the presence of more than one activity.

Figure 9A:
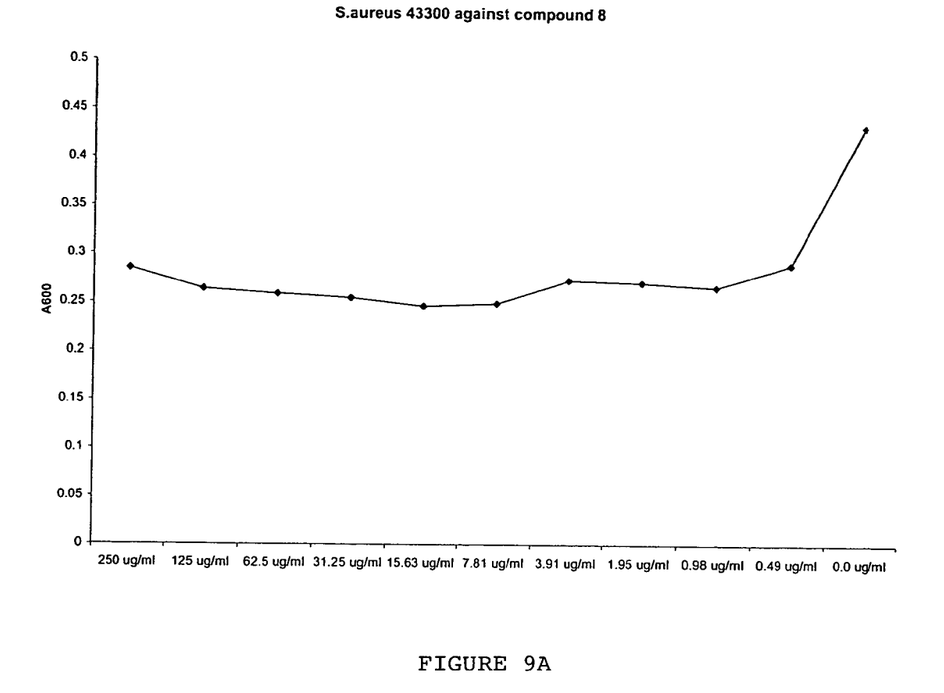
FIGS. 9A to 9C are graphs of bacterial activity as a function of concentration for Compound 8.
Figure 9B:
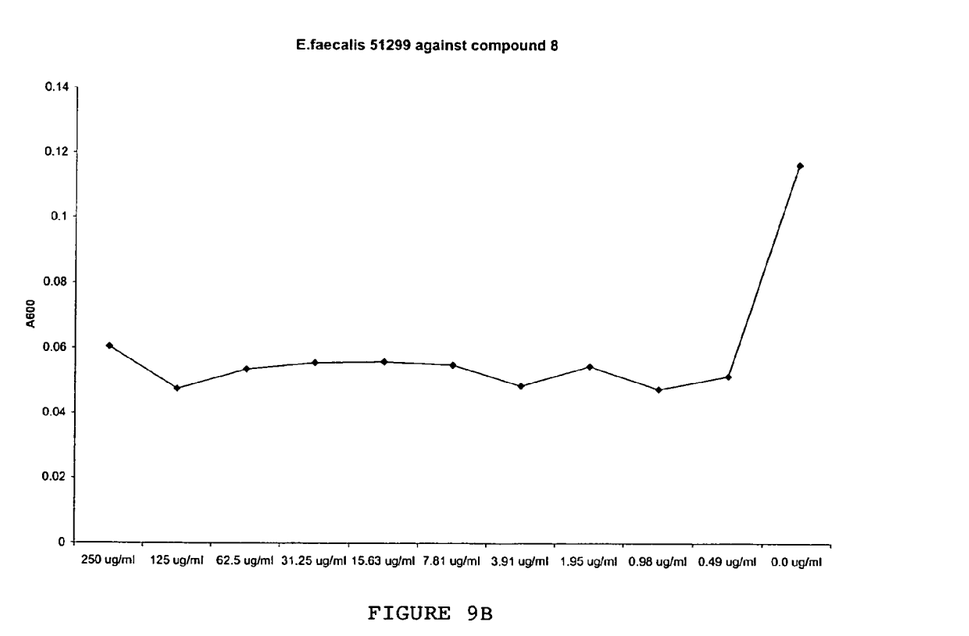
Figure 9C:
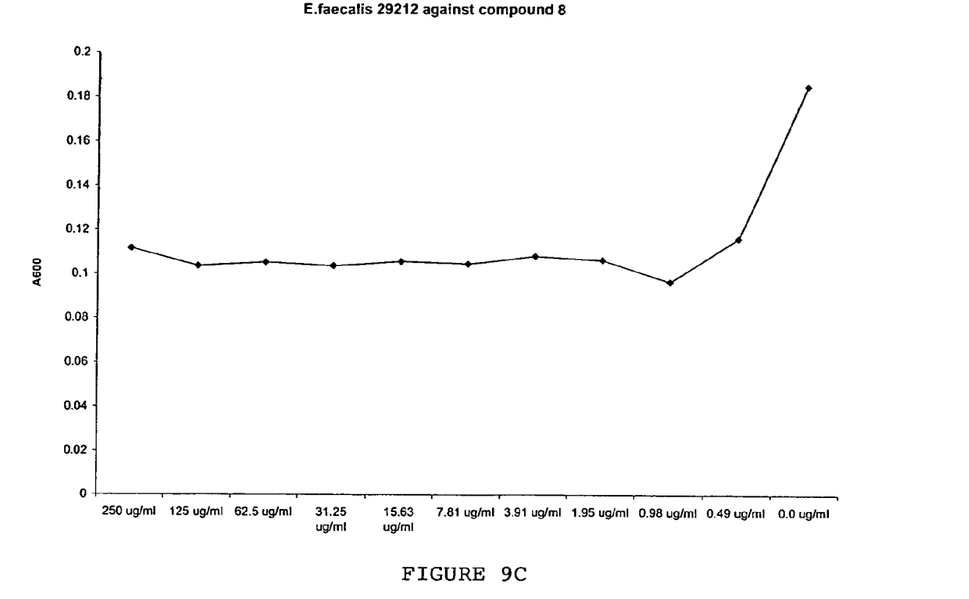

As shown in FIGS. 9A, 9B and 9C, compound 8 was tested for its antibacterial activity against gram-positive bacterial strains *S. aureus* 43300, *E. faecalis* 51299 and *E. faecalis* 29212. It was assayed according to the standard MIC testing procedure for antimicrobials. It showed good inhibition against all three strains at the initial dilute concentration. 50% inhibition were observed at the concentrations of 0.49 µg/ml for *E. faecalis* 51299 and 29212. 70 inhibition was observed at this concentration for *S. aureus* 43300.

The results obtained from the ribosidase inhibition studies with compounds 6, 7 and 8 indicate an important role for the aromatic ring in compounds 6 and 7. The aromatic ring can increase the hydrophobicity of the inhibitor. It can also bind to a region on the enzyme that is normally occupied by the nucleoside base thus enhancing the affinity towards enzyme. This is not present in 8 and can explain its lack of inhibitory power. The increased hydrophobicity should also make it easier for 6 and 7 to penetrate the cell membrane. These enzymes are not extracellular and the fact that the same inhibition was observed for compounds 6 and 7 in both the lysate and whole cell experiments demonstrates that uptake through the cell membrane is not limiting. An evaluation of the activity of these inhibitors against purified ribosidases and related enzymes can be tested. Good candidates are purine nucleoside phosphorylases.

The preparation of 3 new compounds of the thiazine class is described. Two of these compounds (6 and 7) are tetrahydro-1H-pyrrolo-[2,1-c][1,4]benzothiazines with iminopentitol substructures corresponding to the L-lyxo and D-ribo configurations. The compounds were designed to present a favorable transition state mimic based on locking the iminopentitol scaffold into the most desirable conformation as suggested by stereoelectronic configurations (antiperiplanar lone pair requirement). Structures were designed with the aid of molecular mechanics and semi-empirical calculation tools. Structures obtained by X-ray analysis matched those obtained by calculation exactly. The compounds demonstrated good inhibitory activity against β-D-ribosidases present in bacterial cells and cell lysates. The inhibitory activity of the more readily formed but unnatural L-lyxo isomer was comparable to that of the isomer with the natural D-ribo configuration. It was also obtained in much higher yield as expected from steric considerations. The results of the studies with a related compound 8 that lacked the fused aromatic ring indicate that under the conditions explored here, the oxocarbenium surrogate alone is not sufficient. Compound 8 is an intermediate to further compounds. This can indicate an absolute requirement for an aromatic aglycon equivalent or it might represent some physicochemical anomaly involving membrane solubility or partitioning. It should be noted, however, that the crystal structure of one class of nucleoside hydrolases reveals an "aromatic stacking network" in the active site.

The aromatic ring in compounds 6 and 7 present significant opportunities for the further refinement of inhibitor design. They can be further functionalized to provide additional H-bonding donor or acceptor, van der Waals or electrostatic interaction sites leading to a plethora of new inhibitory compounds of biological importance around this scaffold. Although few nucleoside hydrolase inhibitors are known, it is generally accepted that substituted aromatic groups attached to the ring nitrogen of iminopentitols enhance their inhibitory activity.[24] The development of compounds of the new thiazine class described here opens the way to the development of new inhibitors to enzymes of therapeutic importance such as nucleoside hydrolases and purine nucleoside phosphorylases (PNP).

General Procedures

IR spectra were recorded on a Nicolet 710 FT-IR instrument. The $^1$H (and $^{13}$C) NMR spectra were recorded at 500 MHz (125.5 MHz for 13-C) on a Varian VXR spectrometer. The HRMS FAB mass spectra were obtained using a Jeol HX-110 double-focusing mass spectrometer operating in positive ion mode. Structure calculations were carried out using the MM+forcefield followed by geometry optimization using the AM1 method as implemented in the program HYPERCHEM™ (Hypercube, Gainsville, Fla. USA).

Inhibition Assay

Inhibitory potency was determined by spectrophotometrically measuring the residual hydrolytic activities of the bacterial produced β-ribosidase 2. The bacterium used to produce β-ribosidase was *Salmonella* sp.35664, both whole cell and lysed strains. 3',4'-Dihydroxyflavone-4'-β-D-ribofuranoside 15 (DHF-riboside) was used as substrate. The assay was performed in a PBS buffer at pH 7.0, 37° C. Serial dilutions were made of the inhibitors to a final concentration of 0.2µg/µL to 15µg/µL in each assay solution. The strain was grown to mid exponential phase and removed from the media and rediluted in PBS buffer. Inhibition studies were performed by adding each strain to the respective buffer solutions along with DHF-riboside, ferric ammonium citrate and inhibitors. For compound 6 and 7, 10% DMSO solution was used to increase the solubility. The solutions were incubated at 37° C. and the absorbance of the complex formed between released 3',4'-dihydroxyflavone and iron was determined at 387 nm at time 15 min, 30 min, 45 min, 60 min, 75 min, 90 min, 105 min, 2 hours, 2.5 hours, 3.0. hours, 4.0. hours, 4.5 hours, 5 hours, 20 hours, and 24 hours.

Synthesis

Methyl 5-Bromo-5-deoxy-D-ribofuranoside (10) A solution of D-ribose (15 g, 0.1 mol) and hydrochloric acid (15 mL) in methanol (1500 mL) was stirred at room temperature for 20 hours. Sodium carbonate (5 g, 0.06 mol) was added followed by sodium carbonate. The reaction mixture was stirred for 2 hours and two thirds of the solvent was removed on a rotary evaporator at a temperature of less than 30° C. The mixture was filtered and concentrated. The resulting methyl D-riboside 9 was obtained as a yellow oil and was used without further purification. To a stirred solution of 9 (5 g, 30 mmol) in anhydrous pyridine (300 mL) at 0° C. was added triphenylphosphine (16.0 g, 60 mmol) and carbon tetrabromide (18.0 g, 50 mmol). The resulting mixture was protected from moisture and stirred at 0° C. for ten minutes. The mixture was then heated to 65° C. and stirred at this temperature for 6 hours. Methanol (10 mL) was added to decompose any excess reagent. The solvent was removed by evaporation and the residue was dissolved in dichloromethane and was then passed though a pad of silica gel. Dichloromethane was removed by evaporation and the resulting residue was dissolved in toluene and the product was extracted several times with water. Removal of water afforded the expected mixture of methyl 5-Bromo-5-deoxy-α- and β-D-ribofuranoside 10 (6.0 g, 86.7%, α:β=3:1). The mixture was used in the next step without separating the anomers IR (CHCl$_3$) ν$_{max}$ 3387.18, 2933.49, 1121.60, 1088.32, 1025.91 cm$^{-1}$.: Methyl 5-Bromo-5-deoxy-α-D-ribofuranoside $^1$H NMR (500 MHz, D$_2$O) δ 4.86, (1H, s), 4.19-4.13 (2H, m), 4.02 (1H, d, J=5 Hz), 3.64 (1H, dd, J=11, 4.3 Hz), 3.53 (1H, dd, J=11.5, 6.3 Hz), 3.35 (3H, s); $^{13}$C NMR (125.5 MHz, D$_2$O) 108.1, 81.7, 74.6, 73.1, 55.4, 34.2 ppm. Methyl 5-Bromo-5-deoxy-β-D-ribofuranoside $^1$H NMR (500 MHz, D$_2$O) δ 4.97, (1H, d, J=4.5 Hz), 4.22 (1H, m), 3.93 (1H, m), 4.15-4.11 (1H, m), 4.01 (1H, m), 3.57 (2H, m), 3.38 (3H, s); $^{13}$C NMR (125.5 MHz, D$_2$O) 103.7, 83.0, 71.7, 71.0, 55.8, 33.5 ppm.

Methyl 5-Bromo-5-deoxy-2,3-di-O-trimethylacetyl-D-ribofuranoside (11) Pivaloylation of 10 (2.0 g, 8.8 mmol) by trimethylacetyl chloride (4.34 mL, 35.0 mmol) in pyridine (15 mL) at room temperature for 2 days afforded a white solid 11 (3.2 g, 91.1%), IR (CHCl$_3$) ν$_{max}$ 2972.45, 1739.35, 1162.70, 1139.15 cm$^{-1}$. The mixture was used in the oxidation step without separating the anomers: Methyl 5-Bromo-5-deoxy-2,3-di-O-trimethylacetyl-α-D-ribofuranoside $^1$H NMR (500 MHz, CDCl$_3$) δ 5.25, (1H, m), 5.20 (1H, d, J=4.5 Hz), 4.82 (1H, s), 4.28, (1H, m), 3.47 (2H, t, J=6.5 Hz), 3.37 (3H, s), 1.19 (9H, s), 1.16 (9H, s); 13C NMR (125.5 MHz, CDCl$_3$) 177.1, 176.9, 106.2, 80.0, 74.9, 74.05, 55.2, 38.8, 38.7, 33.5, 27.1 ppm. Methyl 5-Bromo-5-deoxy-2,3-di-O-trimethylacetyl-β-D-ribofuranoside $^1$H NMR (500 MHz, CDCl$_3$) δ 5.17, (1H, d, J=4 Hz), 5.04 (1H, m), 4.90 (1H, m), 4.22 (1H, m), 3.64 (1H, dd, J=11, 4 Hz), 3.55 (1H, dd, J=11, 4.5 Hz), 3.35 (3H, s), 1.19 (9H, s), 1.18 (9H, s); $^{13}$C NMR (125.5 MHz, CDCl$_3$) 177.8, 177.5, 101.0, 80.5, 74.1, 72.0, 55.6, 38.8, 38.7, 33.1, 27.1 ppm.

Methyl 5-Bromo-5-deoxy-2,3-di-O-trimethylacetyl-D-erythro-4-pentulosonic acid methyl ester (12) Chromium trioxide (2.43 g, 24.3 mmol) was added to a solution of 11 (3.2 g, 8.1 mmol) in acetic acid (100 mL) and acetic anhydride (10 mL). The suspension was stirred at room temperature for 2 hours. The mixture was then poured slowly into cold water (500 mL). The water solution was extracted 5 times with CH$_2$Cl$_2$ and the combined organic phase was washed with brine, saturated sodium bicarbonate and dried (Na$_2$SO$_4$). The solution was passed through a small pad of silica gel to remove coloration due to chromium salts and dried to give 12 as a colorless oil (3.2 g, 96.2%). IR (CHCl$_3$) ν$_{max}$ 2975.59, 1745.62, 1125.06 cm$^{-1}$. $^1$H NMR (500 MHz, CDCl$_3$) δ 5.86, (1H, d, J=3.0 Hz), 5.70 (1H, d, J=2.5 Hz), 4.08 (1H, d, J=13 Hz), 4.01 (1H, d, J=12.5Hz), 3.76 (3H, s), 1.24 (9H, s), 1.20 (9H, s); $^{13}$C NMR (125.5 MHz, CDCl$_3$) δ 195.6, 176.6, 176.4, 166.7, 74.9, 71.5, 52.9, 38.8, 38.7, 31.3, 26.9 ppm; HRFABMS (M+H$^+$) Calcd. 409.0862, found 409.0863.

Lactams 13 and 14: A solution of 12 (2.0 g, 4.9 mmol) and 2-aminothiophenol (0.73 g, 5.9 mmol) in methanol (150 mL) was stirred at room temperature for one hour, followed by addition of sodium cyanoboronhydride (0.56 g,. 7.3 mmol). The reaction mixture was stirred overnight and concentrated. The resulting residue was dissolved in dichloromethane and sodium carbonate was added to facilitate the lactam cyclization. After stirred for overnight, the suspension was filtered and the dichloromethane solution was washed by brine and dried (Na$_2$SO$_4$), concentrated. The residue was purified by column chromatography (10:1 Hexanes/Ethyl acetate) to yield two lactam diastereomers.

Product 13 (0.71 g, 57.4%) was obtained as a white solid. IR (CHCl$_3$) ν$_{max}$ 2972.76, 1742.61, 1155.27 cm$^{-1}$. $^1$H NMR (500 MHz, CDCl$_3$) δ 8.72 (1H, dd, J=8.5, 1 Hz), 7.14 (1H, dd, J=8, 1.5 Hz), 7.10 (1H, td, J=8, 1.5 Hz), 6.99 (1H, td, J=7.5, 1.5 Hz), 5.72 (1H, t, J=4.8 Hz), 5.65 (1H, d, J=5.5 Hz), 4.32 (1H, m), 3.14 (1H, dd, J=13, 10.5 Hz), 2.88 (1H, dd, J=13, 2.5 Hz), 1.24 (9H, s), 1.21 (9H, s); $^{13}$C NMR (125.5 MHz, CDCl$_3$) δ 177.1, 176.9, 166.8, 133.7, 127.3, 125.8, 124.5, 121.1, 120.4, 69.0, 67.9, 57.4, 39.2, 38.9, 27.2, 27.1, 25.0; HRFABMA (M+H$^+$) Calcd. 406.1689, found 406.1691.

Product 14 (0.13 g, 9.6%) was obtained as an amorphous solid. IR (CHCl$_3$) ν$_{max}$ 2973.71, 1738.05, 1145.55 cm$^{-1}$. $^1$H NMR (500 MHz, CDCl$_3$) δ 8.06 (1H, d, J=8 Hz), 7.15-7.06 (3H, m), 5.63 (1H, t, J=7.5 Hz), 5.51 (1H, d, J=7 Hz), 4.34 (1H, m), 3.17 (1H, t, J=12 Hz), 2.96 (1H, dd, J=13, 2.5 Hz), 1.27 (9H, s), 1.25 (9H, S); $^{13}$C NMR (125.5 MHz, CDCl$_3$) δ 177.4, 177.2, 165.3, 132.2, 126.1, 125.8, 124.8, 123.4, 73.0, 71.3, 54.7, 38.9, 38.7, 27.1, 27.0 ppm; HRFABMA (M+H$^+$) Calcd. 406.1689, found 406.1689.

2(S),3(R),4(S)-dihydroxy-2,3,3a,4-tetrahydro-1H-pyrrolo-[2,1-c][1,4]benzothiazine (6) A solution of lactam 13 (0.40 g, 1.0 mmol) and BH$_3$-THF (3.3 mL, 5.0 mmol) in anhydrous THF (10 mL) was refluxed for 4 hours and the TLC and NMR showed the completion of the reduction. The solvent was removed and methanol was added and concentrated for 3 times. The residue was dissolved in methanol (20 mL), followed by addition of NaOMe (0.20 g, 3.8 mmol). The reaction was stirred for 8 hours and concentrated. The residue was purified by column chromatography (15:1 CH$_2$Cl$_2$/MeOH) to afford a white crystalline solid (0.2 g, 90.9%). m.p. 127-128° C.; IR (CHCl$_3$) ν$_{max}$ 3113.94, 1124.86 cm$^{-1}$. $^1$H NMR (500 MHz, CD$_3$OD) δ 6.93 (2H, d, J=7.5 Hz), 6.48 (1H, td, J=7.5, 1 Hz), 6.41 (1H, d, J=8 Hz), 4.37 (1H, m), 4.11 (1H, t, J=3.8 Hz), 3.80 (1H, dt, J=10.5, 3 Hz), 3.51 (1H, t, J=8.5 Hz), 3.15 (1H, t, J=8.5 Hz), 2.96 (1H, m), 2.85 (1H, dd, J=12.5, 3 Hz); 13C NMR (125.5 MHz, CD$_3$OD) δ 146.6, 130.9, 129.8, 119.7, 119.2, 115.1, 77.1, 74.3, 65.7, 55.8, 28.0 ppm; HRFABMA (M+H$^+$) Calcd. 224.0745, found 224.0745.

2(R)-3(R),4(S)-dihydroxy-2,3,3a,4-tetrahydro-1H-pyrrolo-[2,1-c][1,4]benzothiazine (7) was obtained the same way as compound 6 from lactam 14 (87%) $^1$H NMR (500 MHz, CD$_3$OD) δ 6.99-6.93 (2H, m), 6.51-6.46 (2H, m), 4.18 (1H, d, J=4.5 Hz), 4.07 (1H, d, J=2.5 Hz), 4.01 (1H, m), 3.61 (1H, dd, J=10.5, 5.0 Hz), 3.22 (1H, d, J=10.5 Hz), 2.90 (2H, m); $^{13}$C NMR (125.5 MHz, CD$_3$OD) δ 143.0, 127.0, 126.0, 115.5, 115.1, 110.9, 77.1, 73.8, 60.7, 54.0, 23.6 ppm; HRFABMA (M+H$^+$) Calcd. 224.0745, found 224.0746.

7(S)-hexahydro-8(R),9(S)-bis-trimethylacetoxy-1H-pyrrolo-[1,4]-thiazin-6-one (15) and its isomer 7(S)-hexahydro- 8(R),9(R)-bis-trimethylacetoxy-1H-pyrrolo-[1,4]-thiazin-6-one: A solution of 12 (0.8 g, 2.0 mmol), HS(CH$_2$)$_2$NH$_2$ (0.18 g, 2.3 mmol) and NaCNBH$_3$ (0.18 g, 2.9 mmol) in methanol (50 mL) was stirred at room temperature for 24 hours and then concentrated. The resulting residue was dissolved in dichloromethane and washed with brine, dried (Na$_2$SO$_4$) and concentrated. Compound 15 and its isomer were isolated by column chromatography (4:1 Hexanes/Ethyl acetate).

7(S)-hexahydro-8(R),9(S)-bis-trimethylacetoxy-1H-pyrrolo-[1,4]-thiazin-6-one (15) was obtained as a white solid (0.40 g, 57%). %), m.p. 118-220° C. IR (CHCl$_3$) $v_{max}$ 1739.61, 1705.31, 1141.03 cm$^{-1}$. $^1$H NMR (500 MHz, CDCl$_3$) δ 5.50 (1H, t, J=5 Hz), 5.43 (1H, dd, J=6, 1.5 Hz), 4.43 (1H, dt, J=13.5, 2.8 Hz), 3.88 (1H, m), 2.97 (1H, m), 2.72-2.64 (2H, m), 2.52 (1H, m), 2.40 (1H, dt, J=13.5, 2.5 Hz), 1.21 (9H, s), 1.20 (9H, s); $^{13}$C NMR (125.5 MHz, CDCl$_3$) δ 177.0, 176.9, 167.7, 68.8, 67.5, 57.7, 42.2, 39.1, 38.8, 27.3, 27.2, 27.1, 27.0 ppm; HRFABMA (M+H$^+$) Calcd. 358.1689, found 358.1685.

7(S)-hexahydro-8(R),9(R)-bis-trimethylacetoxy-1H-pyrrolo-[1,4]-thiazin-6-one was obtained as a white solid (0.12 g, 20%). m.p. 138-139° C.; IR (CHCl$_3$) $v_{max}$ 1739.70, 1717.38, 1160.52, 1136.98 cm$^{-1}$. $^1$H NMR (500 MHz, CDCl$_3$) δ 5.34 (1H, d, J=7 Hz), 5.09 (1H, dd, J=7, 2.3 Hz), 4.44 (1H, dt, J=13.5, 2.8 Hz), 3.60 (1H, dt, J=11, 2.5 Hz), 3.02 (1H, m), 2.75 (1H, d, J=13 Hz), 2.62-2.51 (2H, m), 2.42 (1H, m), 1.20 (9H, s), 1.16 (9H, s); $^{13}$C NMR (125.5 MHz, CDCl$_3$) δ 177.4, 177.1, 166.6, 70.1, 68.2, 62.3, 42.2, 38.8, 38.8, 30.1, 27.1, 27.0, 26.4 ppm; HRFABMA (M+H$^+$) Calcd. 358.1689, found 358.1688.

7(S)-8(R),9(S)-dihydroxy-hexahydro-1H-pyrrolo-[1,4]-thiazine (8) A solution of lactam 15 (0.24 g, 0.67 mmol) and BH$_3$-THF (2.2 mL, 3.4 mmol) in anhydrous THF (10 mL) was refluxed for 3 hours and the TLC and NMR showed the completion of the reduction. The solvent was removed and methanol was added and concentrated for 3 times. The residue was dissolved in methanol (20 mL), followed by addition of NaOMe (0.10 g, 1.9 mmol). The reaction was stirred for 8 hours and concentrated. The residue was applied to an ion exchange column (Dowex 50WX8-400, 5 g), which was washed with water (30 mL) and eluted with 2N NH$_4$OH (30 mL). The eluent was concentrated and yielded a white crystalline solid (0.1 g, 85.0%). m.p. 92-93° C. $^1$H NMR (500 MHz, D$_2$O) δ 4.23 (1H, m), 4.07 (1H, m), 3.22 (1H, dt, J=12, 2.5 Hz), 2.86-2.74 (3H, m), 2.52 (1H, dt, J=13.5, 3 Hz), 2.49 (1H, m), 2.44 (1H, m), 2.33-2.25 (2H, m); $^{13}$C NMR (125.5 MHz, D$_2$O) δ 71.9, 67.4, 67.0, 60.9, 53.9, 26.4, 26.3 ppm; HRFABMA (M+H$^+$) Calcd. 176.0745, found 176.0745.

REFERENCES (1) Versees, W.; Decanniere, K.; Pelle, R.; Depoorter, J.; Brosens, E.; Parkin, D. W.; Steyaert, J. *J Mol. Biol.*, 2001 307(5) 1363-1379.

(2) Petersen, C.; Birk Møller, L. *J. Biol. Chem.*, 2001 276(2), 884-894.

(3) Deslongchamps, P. *Stereoelectronic Effects in Organic Chemistry*. Pergamon Press, Oxford, 1983.

(4) D. L. Zechel and S. G. Withers, *Acc. Chem. Res.*, 2000, 33, 11;

(5) T. D. Heightman and A. T. Vasella, *Angew. Chem., Int. Ed.*, 1999, 38, 750

(6) Edwige Lorthiois, Muthuppalaniappan Meyyappan and Andrea Vasella *Chem. Commun.*, 2000, 1829-1830

(7) Gopaul, D. N.; Meyer, S. L.; Degano, M.; Sacchettini, J. C.; Schramm, V. L. *Biochemistry* 1996, 35, 5963-5970.

(8) Mazzella, L. J.; Parkin, D. W.; Tyler, P. C.; Furneaux, R. H.; Schramm, V. L. *J. Am. Chem. Soc.* 1996, 118, 2111-2112.

(9) Parkin, D. W.; Limberg, G.; Tyler, P. C.; Furneaux, R. H.; Chen, X. Y.; Schramm, V. L. *Biochemistry* 1997, 36, 3528-3534.

(10) Tao, W., Grubmeyer, C., Blanchard, J. S. *Biochemistry* 1996, 35, 14-21.

(11) Kline, P. C.; Schramm, V. L. *Biochemistry* 1992, 31, 5964-5973.

(12) Kline, P. C.; Schramm, V. L. *Biochemistry* 1993, 32, 13212-13219.

(13) Kline, P. C.; Schramm, V. L. *Biochemistry* 1995, 34, 1153-1162.

(14) Fedorov, A.; Shi, W.; Kicska, G.; Fedorov, E.; Tyler, P. C.; Furneaux, R. H.; Hanson, J. C.; Gainsford, G. J.; Larese, J. Z.; Schramm, V. L.; Almo, S. C. *Biochemistry* 2001, 40, 853-860.

(15) Miles, R. W.; Tyler, P. C.; Furneaux, R. H.; Bagdassarian, C. K.; Schramm, V. L. *Biochemistry* 1998, 37, 8615-8621.

(16) Evans, G. B.; Furneaux, R. H.; Gainsford, G. J.; Schramm, V. L.; Tyler, P. C. *Tetrahedron* 2000, 56, 3053-3062.

(17) Yasuda, K.; Kizu, H.; Yamashita, T.; Kameda, Y.; Kato, A.; Nash, R. J.; Fleet, G. W. J.; Molyneux, R. J.; Asano, N. *J. Nat. Prod.* 2002, 65, 198-202.

(18) Asano, N.; Yamashita, T.; Yasuda, K.; Ikeda, K.; Kizu, H.; Kameda, Y.; Kato, A.; Nash, R. J.; Lee, H. S.; Ryu, K. S. *Journal of Agricultural and Food Chemistry* 2001, 49, 4208-4213.

(19) Asano, N.; Yasuda, K.; Kizu, H.; Kato, A.; Fan, J. Q.; Nash, R. J.; Fleet, G. W. J.; Molyneux, R. J. *Eur. J. Biochem.* 2001, 268, 35-41.

(20) Fleet, G. W. J.; Nicholas, S. J.; Smith, P. W.; Evans, S. V.; Fellows, L. E.; Nash, R. J. *Tetrahedron Lett.* 1985, 26, 3127-3130.

(21) Angyal, S. J.; James, K. *Australian Journal of Chemistry* 1970, 23, 1209.

(22) Pistia, G.; Hollingsworth, R. I.; *Carbohydrate Research* 328, 23, 467-472.

(23) Butterworth, L. A., J. D.; Davies, G.; Burton, M.; Reed, R. H.; Gould, F. K. *Journal of Applied Microbiology* 2004, 96, 170-176.

(24) Miles, R. W.; Tyler, P. C.; Evans, G. B.; Furneaux, R. H.; Parkin, D. W.; Schramm, V. L. *Biochemistry* 1999 38(40) 13147-13154.

It is intended that the foregoing description be only illustrative of the present invention and that the present invention be limited only by the hereinafter appended claims.

I claim:

1. A 1H-pyrrolo-1,4-thiazine compound of the formula wherein R$_1$ and R$_2$ are individually selected from the group consisting of hydrogen, and alkyl containing 1 to 6 carbon atoms which alkyl carbon atoms can be substituted with a halogen group, or alternatively R$_1$ and R$_2$ together with carbon atoms to which they are attached to form a benzene ring which benzene ring can be substituted with a halogen.

2. 3,4-dihydroxy,2,3,3a-4-tetrahydro-1-H-pyrrolo-[2,1c][1,4]benzothiazine.

3. 2(S), 3(R), 4(S)-3,4-dihydroxy-1,3,3a,4-tetrahydro-1H-pyrrolo-[2,1-c][1,4]benzothiazine.

4. 2(R)-3(R),4(S)-3,4-dihydroxy-2,3,3a,4-tetrahydro-1H-pyrrolo-[2,1c][1,4]benzothiazine.

5. 7(S)-8(R),9(S)-3,4-dihydroxy-hexahydro-1H-pyrrolo[1,4]-thiazine.

6. A process for the preparation of a 3,4-dihydroxy-1H-pyrrolo-1, 4-thiazine which comprises:
   (a) reacting 5-bromo-5 deoxy-2,3-di-O-protected groups 4pentulosonic acid lower alkyl containing 1 to 6 carbon atoms ester with an amino aliphatic or aromatic thiol containing 4 to 6 carbon atoms in a solvent and with a reducing agent to form the 3,4-dihydroxy-1H-pyrrolo-1,4-thiazine in a reaction mixture; and
   (b) separating the 3,4-dihydroxy-1H-pyrrolo-1,4-thiazine from the reaction mixture.

7. A process for the preparation of a compound which is a 3,4-dihydroxy-1H-pyrrolo-1,4-thiazine according to claim 1 which comprises:
   (a) reacting at a temperature between about 0° C. and 100° C. 5-bromo-5-deoxy-2,3-di-O-protected-4-pentulosonic acid methyl ester with 2-aminothiophenol or 2-aminothioethane in a solvent containing a reducing agent to produce a protected pyrrolo-1,4-thiazine; and
   (b) deprotecting the protected pyrrolo 1,4thiazine to produce the 3,4-dihydroxy-1H-pyrrolo-1,4-thiazine.

8. The process of claim 7 wherein the protected pentulosonic acid methyl ester is derived from ribose.

9. The process of claim 7 wherein the compound is 3,4-dihydroxy,2,3,3a-4'-tetrahydro-1H-pyrrolo-[2,1c][1,4]benzothiazine.

10. The process of claim 7 wherein the compound is 2(S), 3(R), 4(S)-3,4-dihydroxy-1,3,3a,4-tetrahydro-1H-pyrrolo-[2,1-c][1,4]benzothiazine.

11. The process of claim 7 wherein the compound is 2(R)-3(R),4(S)-dihydroxy-2,3,3a,4-tetrahydro-1H-pyrrolo-[2,1-c][1,4]benzothiazine.

12. The process of claim 7 wherein the compound is 7(S)-8(R),9(S)-3,4-dihydroxy-hexahydro-1H-pyrrolo[1,4]thiazine.

13. 3,4-dihydroxy-2,3,3a, 4-tetrahydro-1H-pyrrolo[1,4]-thiazine.

14. The process of claim 7 wherein the compound is 3,4-dihydroxy-2,3,3a,4-tetrahydro-1H-pyrrolo-[1,4]thiazine.

\* \* \* \* \*

UNITED STATES PATENT AND TRADEMARK OFFICE
CERTIFICATE OF CORRECTION

PATENT NO. : 7,579,343 B2
APPLICATION NO. : 11/516317
DATED : August 25, 2009
INVENTOR(S) : Rawle Hollingsworth and Li Gao Page 1 of 1

It is certified that error appears in the above-identified patent and that said Letters Patent is hereby corrected as shown below:

Column 11, lines 45-63, " " should be -- --.

Column 14, line 50, "β-ribosidase 2." should be --β-ribosidase 21.--.

Column 15, line 40, "(15 mL)" should be --(150 mL)--.

Column 15, line 47, "13C NMR" should be --$^{13}$C NMR--.

Column 16, line 34, "(9H, S)" should be --(9H, s)--.

Column 16, line 54, "13C NMR" should be --$^{13}$C NMR--.

Column 20, line 3, Claim 7, "1,4thiazine to" should be --1,4-thiazine to--.

Column 20, line 17, Claim 12, "[1,4]thiazine" should be --[1,4]-thiazine--.

Column 20, line 22, Claim 14, "[1,4]thiazine" should be --[1,4]-thiazine--.

Signed and Sealed this

Fifth Day of January, 2010

David J. Kappos
*Director of the United States Patent and Trademark Office*